United States Patent
Blad

(10) Patent No.: US 10,858,266 B2
(45) Date of Patent: *Dec. 8, 2020

(54) PORTABLE WATER PURIFICATION SYSTEMS AND METHOD OF ASSEMBLING SAME

(71) Applicant: Steven J. Blad, Arrington, TN (US)

(72) Inventor: Steven J. Blad, Arrington, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/688,056

(22) Filed: Aug. 28, 2017

(65) Prior Publication Data

US 2019/0062177 A1  Feb. 28, 2019

(51) Int. Cl.
| | | |
|---|---|---|
| *A61L 2/20* | (2006.01) | |
| *A61L 9/20* | (2006.01) | |
| *C02F 1/00* | (2006.01) | |
| *C02F 1/32* | (2006.01) | |
| *C02F 1/78* | (2006.01) | |

(Continued)

(52) U.S. Cl.
CPC .............. *C02F 1/002* (2013.01); *A61L 2/202* (2013.01); *A61L 9/20* (2013.01); *B01J 21/06* (2013.01); *C01B 13/10* (2013.01); *C02F 1/28* (2013.01); *C02F 1/325* (2013.01); *C02F 1/78* (2013.01); *C02F 2201/002* (2013.01);

(Continued)

(58) Field of Classification Search
None
See application file for complete search history.

(56) References Cited

U.S. PATENT DOCUMENTS 4,296,328 A * 10/1981 Regan ..................... C02F 1/325
  250/432 R
5,106,495 A *  4/1992 Hughes .................... C02F 1/78
  210/139

(Continued)

FOREIGN PATENT DOCUMENTS

| WO | 2008130710 A1 | 10/2008 | |
|---|---|---|---|
| WO | 2015063581 A1 | 5/2015 | |
| WO | WO-2016174667 A1 * | 11/2016 | ............. C01B 13/10 |

OTHER PUBLICATIONS

International Search Report and Written Opinion, dated Jul. 16, 2018, for related International application No. PCT/US2018/034627.

(Continued)

*Primary Examiner* — Bradley R Spies
(74) *Attorney, Agent, or Firm* — Armstrong Teasdale LLP

(57) ABSTRACT

A portable liquid filtration device includes a portable housing, an inlet configured to receive non-potable water, and an ozone chamber positioned within the portable housing. The ozone chamber is configured to generate an ozone gas from received air. The device also includes a filtration duct positioned within the portable housing and downstream from the inlet. The filtration duct includes at least one advanced oxidation (AO) chamber configured to mix the received water with the ozone gas, and at least one ultraviolet (UV) chamber downstream from the at least one AO chamber and including a UV lamp positioned adjacent the water within the filtration duct. The device further includes an outlet positioned on the portable housing and downstream from the filtration duct. The filtration duct is operable to output at least 200 liters per hour of the received water from the outlet as potable water.

20 Claims, 7 Drawing Sheets

(51) Int. Cl.
  *B01J 21/06* (2006.01)
  *C01B 13/10* (2006.01)
  *C02F 1/28* (2006.01)

(52) U.S. Cl.
  CPC .............. *C02F 2201/008* (2013.01); *C02F 2201/3223* (2013.01); *C02F 2201/782* (2013.01); *C02F 2303/04* (2013.01)

(56) References Cited

U.S. PATENT DOCUMENTS

| | | | |
|---|---|---|---|
| 5,393,419 A | 2/1995 | Tiede et al. | |
| 5,427,693 A | 6/1995 | Mausgrover et al. | |
| 5,433,848 A | 7/1995 | Platter et al. | |
| 6,558,537 B1* | 5/2003 | Herrington | B01D 61/04 210/192 |
| 6,716,343 B2 | 4/2004 | Kool et al. | |
| 6,814,876 B1* | 11/2004 | Neal | C02F 1/32 210/748.12 |
| 7,033,506 B2 | 4/2006 | LeJeune | |
| 7,135,106 B2* | 11/2006 | Marquis | C01B 13/10 210/97 |
| 8,728,310 B1 | 5/2014 | Tjutjunnik | |
| 8,808,537 B1 | 8/2014 | Livingston | |
| 9,073,762 B2 | 7/2015 | Cummins | |
| 2001/0040122 A1* | 11/2001 | Barnes | C02F 1/78 210/123 |
| 2004/0168989 A1* | 9/2004 | Tempest, Jr. | C02F 1/78 210/760 |
| 2009/0041617 A1* | 2/2009 | Lee | A61L 2/208 422/4 |
| 2009/0071331 A1* | 3/2009 | Gillette | A23L 3/358 95/91 |
| 2009/0084734 A1 | 4/2009 | Yencho | |
| 2009/0178968 A1 | 7/2009 | Cummins | |
| 2010/0025337 A1 | 2/2010 | Yencho | |
| 2012/0085691 A1* | 4/2012 | Cummins | C02F 9/00 210/192 |
| 2012/0186658 A1 | 7/2012 | Kuennen et al. | |
| 2014/0094975 A1 | 4/2014 | Nielsen | |
| 2014/0353256 A1 | 12/2014 | Kaschek et al. | |
| 2017/0137304 A1 | 5/2017 | Adams et al. | |
| 2018/0141838 A1* | 5/2018 | Ben-Shalom | C02F 1/008 |

OTHER PUBLICATIONS

Szabo, J. Disinfection of biological agents in the field using a mobile advanced oxidation process, Sep. 2016, EPA/600/R-16/112, USEPA Office of Research and Development, Cincinnati, Ohio USA.

* cited by examiner

PORTABLE WATER PURIFICATION SYSTEMS AND METHOD OF ASSEMBLING SAME

BACKGROUND

The field of the disclosure relates generally to water purification systems, and more particularly to a portable, self-contained water purification device.

In at least some areas of the world, availability of potable water supplies are minimal or nonexistent. The need for potable water in a particular area may arise from a lack of naturally present potable water, from a natural disaster such as an earthquake or a flood that results in contamination of the water supply, or from some variety of accidental contamination. Additionally, extended periods of outdoor presence associated with activities such as hiking, mountain biking, hunting, and back-country skiing make it difficult to carry enough drinking water for personal use and necessitate the use of locally available water supplies, which may contain a variety of chemical and biological contaminants.

At least some known water purification systems include at least one filter and a pump to move water through the filter. Some known water purification systems include multiple filtration steps including introducing ozone to the water and exposing the water to ultraviolet light. However, at least some of these systems are not designed to remove both chemical and biological contaminants such as pesticides and infectious disease carriers. Additionally, at least some water purification systems have a weight or bulk that prevents or inhibits transportation to areas of need, and/or power requirements that prevent or inhibit use at areas of need.

BRIEF DESCRIPTION

In one aspect, a portable liquid filtration device is provided. The portable liquid filtration device includes a portable housing, an inlet positioned on the portable housing and configured to receive non-potable water therethrough, and an ozone chamber positioned within the portable housing. The ozone chamber is configured to receive air from outside the portable housing and generate an ozone gas from the received air. The portable liquid filtration device also includes a filtration duct positioned within the portable housing and in downstream fluid communication with the inlet. The filtration duct includes at least one advanced oxidation (AO) chamber configured to mix the received water with the ozone gas from the ozone chamber, and at least one ultraviolet (UV) chamber in downstream flow communication with the at least one AO chamber and including a UV lamp positioned adjacent the water within the filtration duct. The UV lamp is configured to irradiate the water with UV light. The portable liquid filtration device further includes an outlet positioned on the portable housing and in downstream flow communication with the filtration duct. The filtration duct is operable to output at least 200 liters per hour of the received water from the outlet as potable water.

In another aspect, a method of making a portable liquid filtration device is provided. The method includes positioning an inlet on a portable housing, the inlet configured to receive non-potable water. The method also includes positioning an ozone chamber within the portable housing, the ozone chamber configured to receive air from outside the portable housing and generate an ozone gas from the received air. The method further includes positioning a filtration duct within the portable housing and in downstream fluid communication with the inlet. The filtration duct includes at least one AO chamber configured to mix the received water with the ozone gas from the ozone chamber, and at least one UV chamber in downstream flow communication with the at least one AO chamber and including a UV lamp positioned adjacent the water within the filtration duct. The UV lamp is configured to irradiate the water with UV light. The method additionally includes positioning an outlet on the portable housing and in downstream flow communication with the filtration duct. The filtration duct is operable to output at least 200 liters per hour of the received water from the outlet as potable water.

DETAILED DESCRIPTION

The embodiments described herein overcome at least some of the disadvantages of known water purification systems. The embodiments include a portable liquid filtration device including a portable housing, an inlet, an ozone chamber, a filtration duct including at least one advanced oxidation (AO) chamber and at least one ultraviolet (UV) chamber, and an outlet. The least one AO chamber and the at least one UV chamber cooperate to sanitize the received water. More specifically, the at least one AO chamber mixes the received water with ozone gas from the ozone chamber, and the at least one UV chamber irradiates the received water with UV light. The filtration duct produces potable water at an output of 200 liters per hour or more. In some embodiments, the device weighs no more than 50 pounds and/or occupies no more than four cubic feet, or even no more than two cubic feet.

Unless otherwise indicated, approximating language, such as "generally," "substantially," and "about," as used herein indicates that the term so modified may apply to only an approximate degree, as would be recognized by one of ordinary skill in the art, rather than to an absolute or perfect degree. Accordingly, a value modified by a term or terms such as "about," "approximately," and "substantially" is not to be limited to the precise value specified. In at least some instances, the approximating language may correspond to the precision of an instrument for measuring the value. Additionally, unless otherwise indicated, the terms "first," "second," etc. are used herein merely as labels, and are not intended to impose ordinal, positional, or hierarchical requirements on the items to which these terms refer. Moreover, reference to, for example, a "second" item does not require or preclude the existence of, for example, a "first" or lower-numbered item or a "third" or higher-numbered item. As used herein, the term "upstream" refers to an inlet end or inlet area of a component of a portable liquid purification device, and the term "downstream" refers to an outlet end or outlet area of a component of a portable liquid purification device.

Figure 1:
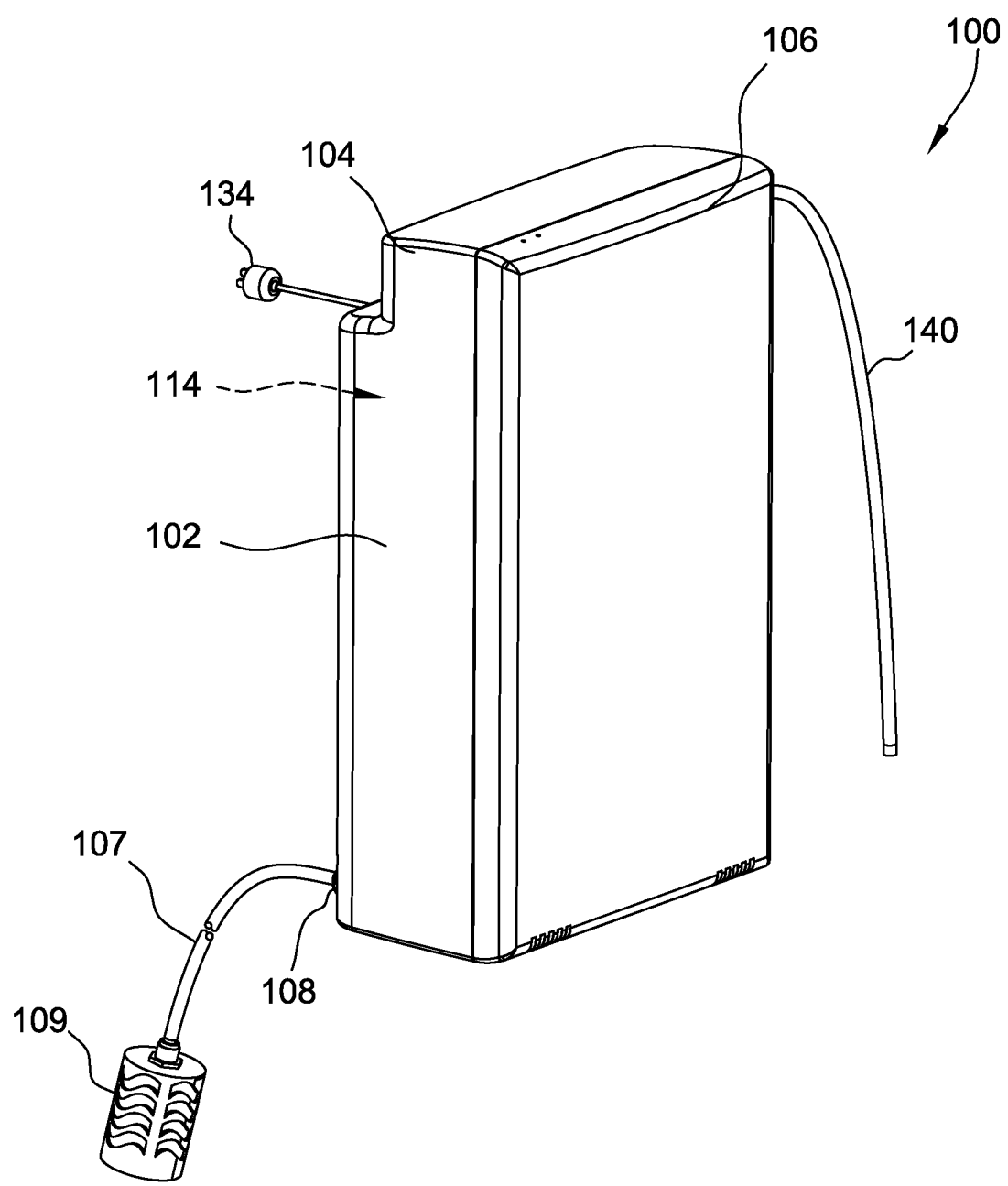
FIG. 1 is a perspective view of an exemplary portable liquid filtration device.
Figure 2:
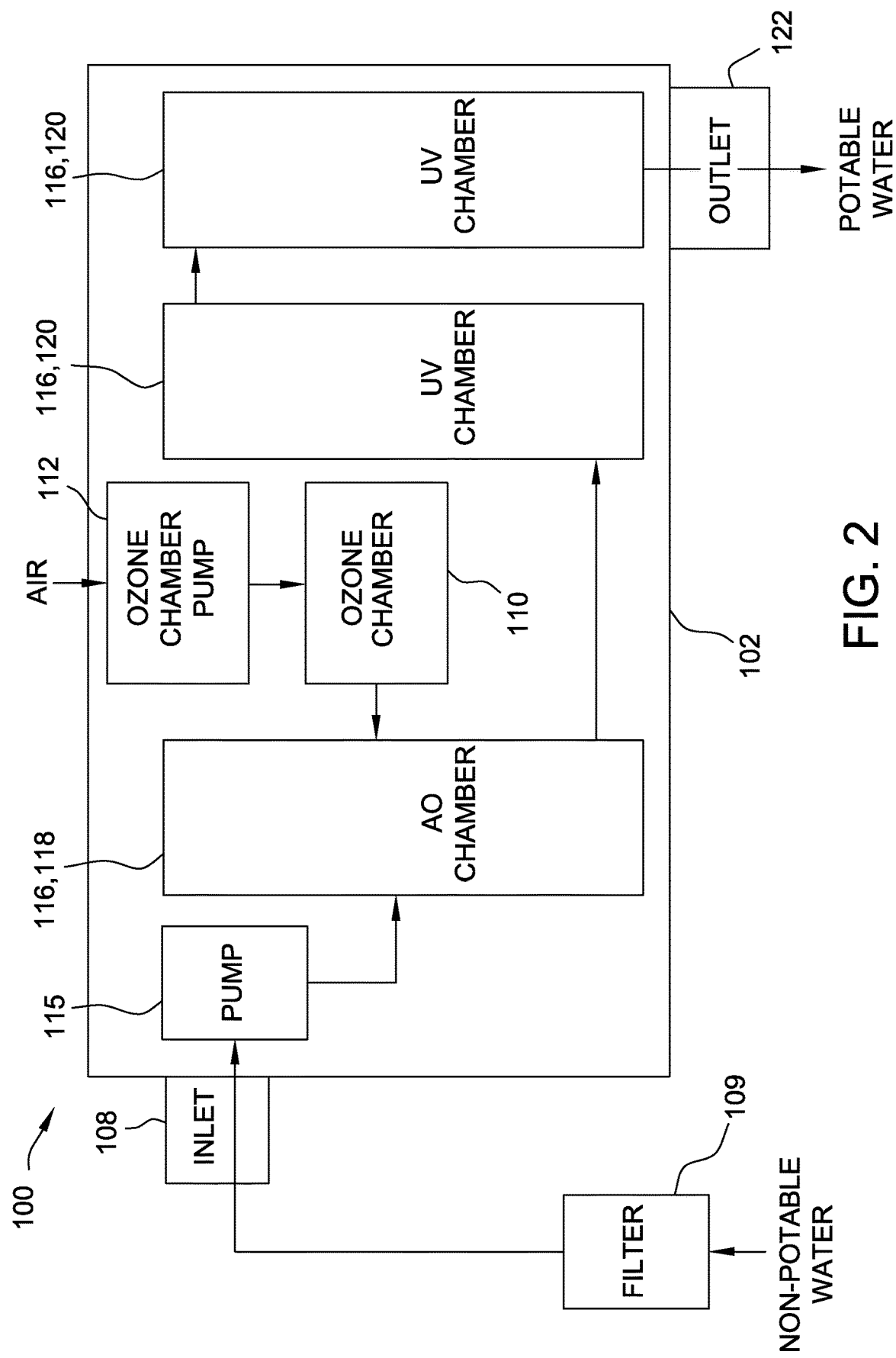
FIG. 2 is a block diagram of the portable liquid filtration device shown in FIG. 1.

FIG. 1 is a perspective view of an exemplary portable liquid filtration device 100. FIG. 2 is a block diagram of the portable liquid filtration device shown in FIG. 1. With reference to FIGS. 1-2, in the exemplary embodiment, portable liquid filtration device 100 includes a portable housing 102 including a front cover 104 and a back cover 106, and an inlet 108 positioned on and extending through portable housing 102.

In the exemplary embodiment, inlet 108 is configured to receive non-potable water and to channel the non-potable water to a filtration assembly 114 housed within portable housing 102. Filtration assembly 114 includes a filtration duct 116 in downstream fluid communication with inlet 108, an ozone chamber 110 positioned within portable housing 102 and configured to provide ozone to filtration duct 116, and an outlet 122 positioned on and extending through portable housing 102 and in downstream flow communication with filtration duct 116. In alternative embodiments, portable liquid filtration device 100 further includes any other component that enables portable liquid filtration device 100 to function as described herein.

In the exemplary embodiment, filtration device 100 also includes a sediment filter 109 in upstream flow communication with inlet 108. Sediment filter 109 is configured to remove particulates from the non-potable water channeled through inlet 108. A flexible inlet tube 107 extends between inlet 108 and sediment filter 109. In alternative embodiments, filtration device 100 does not include sediment filter 109.

In the exemplary embodiment, filtration duct 116 includes an advanced oxidation (AO) chamber 118 and a pair of ultraviolet (UV) chambers 120 coupled together in serial flow communication. An ozone chamber pump 112 is configured to draw air from outside portable housing 102 and channel the air to ozone chamber 110. Ozone chamber 110 is configured to generate an ozone gas from the received air, and channel the ozone gas to AO chamber 118. In the exemplary embodiment, ozone chamber 110 generates the ozone gas via a high voltage discharge into the air received from pump 112. In another embodiment, ozone chamber 110 generates the ozone gas via ultraviolet radiation of the air received from pump 112, for example using a dedicated ozone-generating UV lamp that produces radiation at 185 nanometers wavelength. In alternative embodiments, ozone chamber 110 generates the ozone gas in any suitable fashion that enables filtration device 100 to function as described herein.

Water received through inlet 108 is channeled into AO chamber 118, flows through AO chamber 118 while mixing with the generated ozone gas, and is channeled into a first of UV chambers 120 that is in downstream flow communication with AO chamber 118. After exiting the first of UV chambers 120, the water is channeled into a second of UV chambers 120, flows through the second of UV chambers 120, and is channeled through outlet 122 as potable water. A pump 115 is in serial flow communication with filtration duct 116 and inlet 108 to draw in water. In alternative embodiments, the components of filtration duct 116 may be arranged in any configuration that enables portable liquid filtration device 100 to function as described herein.

In some embodiments, waste is generated as the water flows through filtration duct 116, and the waste is discharged along with a portion of the received water from at least one liquid waste discharge port 128 (shown in FIG. 7) on portable housing 102. For example, the waste is separated from the primary flow through filtration duct 116 due to a relatively heavier weight and/or a higher momentum of the waste as the flow is channeled through a turn in the flow path through filtration duct 116, and is channeled to liquid waste discharge port 128. In alternative embodiments, waste is not generated in sufficient amounts in filtration duct 116 to merit discharge.

Figure 3:
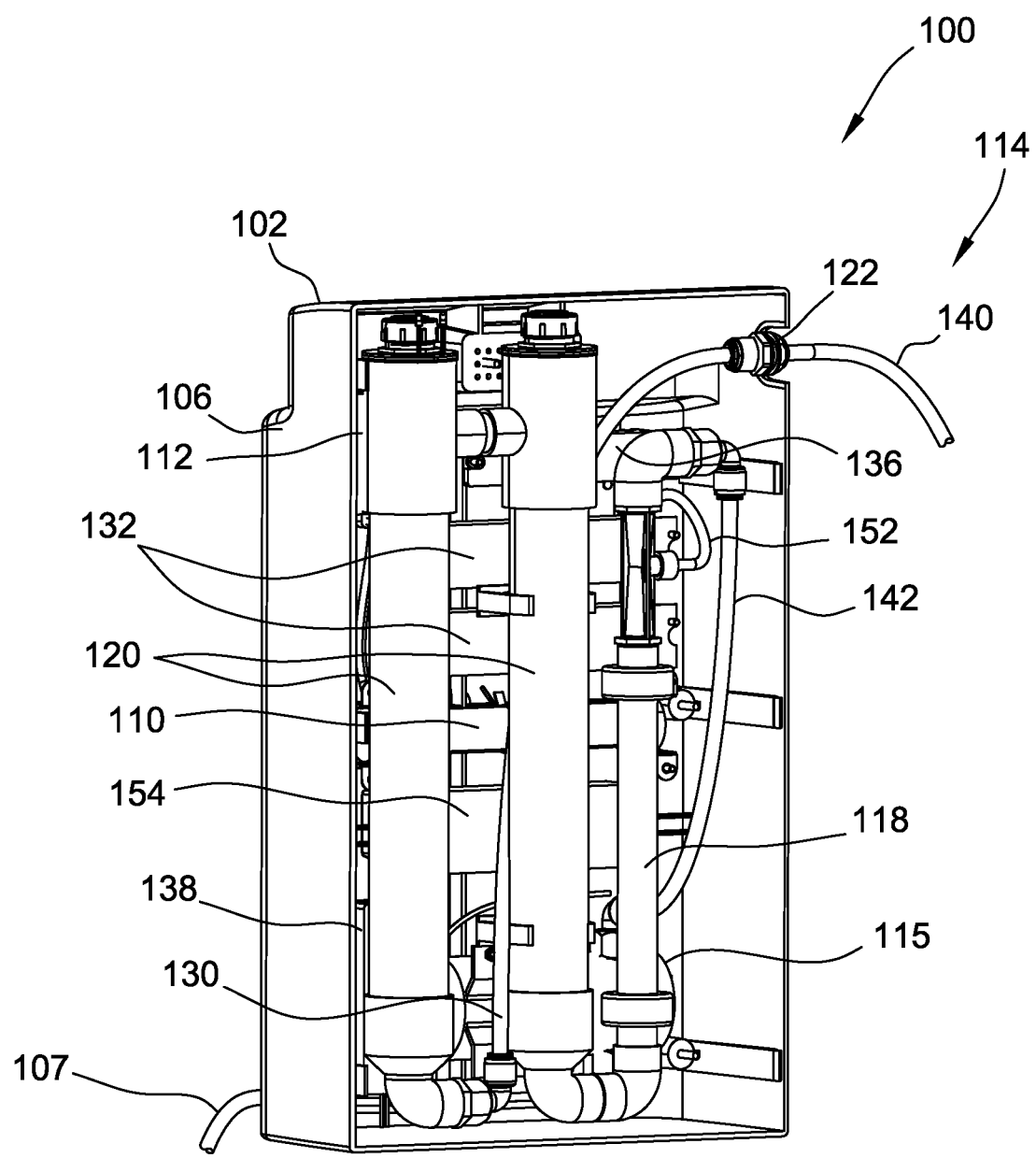
FIG. 3 is a sectional perspective view of a portion of the portable liquid filtration device shown in FIG. 1 illustrating an exemplary filtration assembly.
Figure 4:
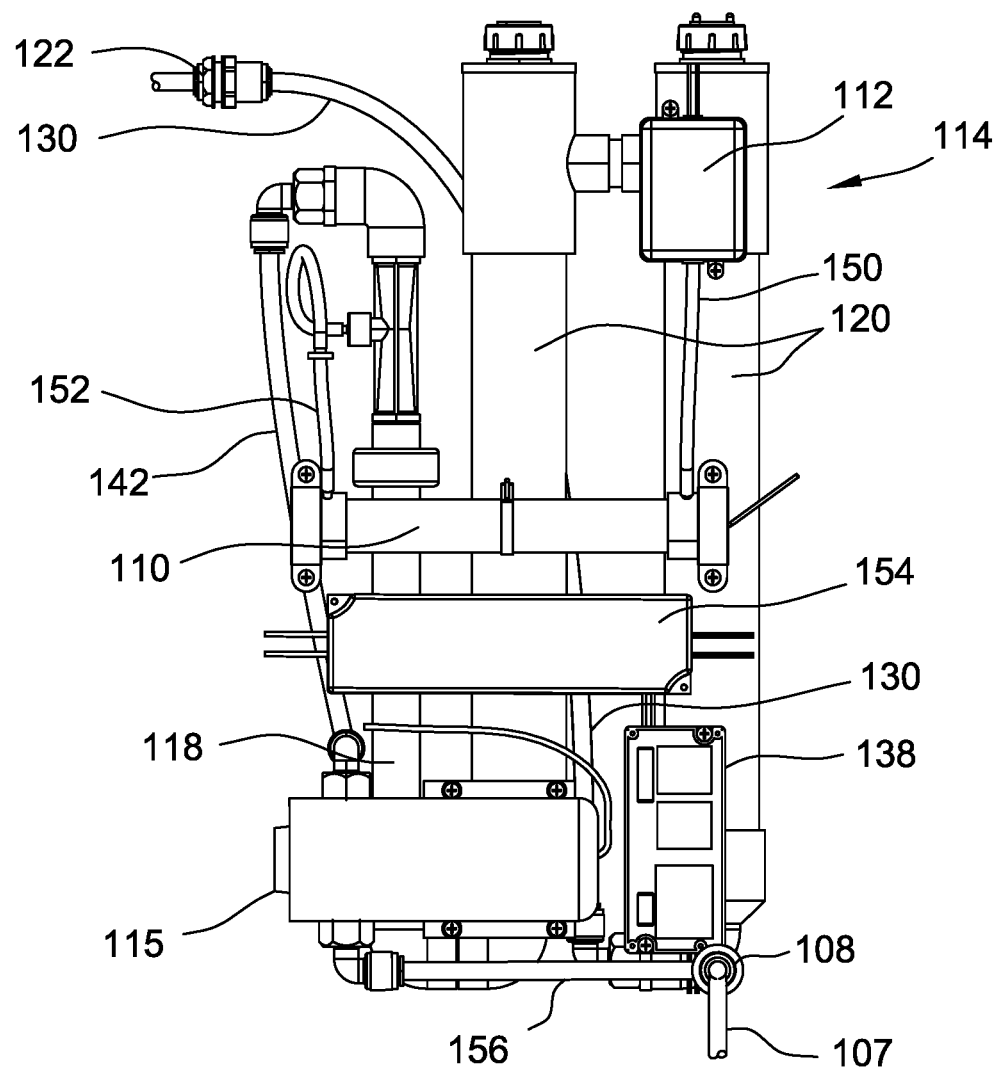
FIG. 4 is a back view of the filtration assembly shown in FIG. 3.

FIG. 3 is a sectional perspective view of a portion of portable liquid filtration device 100 (shown in FIG. 1) illustrating an exemplary arrangement of filtration assembly 114 within portable housing 102. FIG. 4 is a back view of selected components of filtration assembly 114 (shown in FIG. 3). With reference to FIGS. 1-4, filtration assembly 114 also includes connecting flow channels between AO chamber 118, UV chambers 120, and associated components. In the exemplary embodiment, the received air is channeled through a flexible air delivery tube 150 from ozone chamber pump 112 to ozone chamber 110. Similarly, ozone gas generated by ozone chamber 110 is channeled to AO chamber 118 through an ozone delivery tube 152. The received non-potable water is channeled from inlet 108 to pump 115 through a pump inlet tube 156. The received water is discharged from pump 115 and is channeled to AO chamber 118 through a pump outlet tube 142. After flowing through AO chamber 118 and each UV chamber 120, potable water is discharged from the second of UV chambers 120 and is channeled to outlet 122 through a UV chamber discharge tube 130. In alternative embodiments, filtration assembly 114 includes any suitable connecting flow channels that enable portable liquid filtration device 100 to function as described herein.

In the exemplary embodiment, filtration assembly 114 further includes a pair of UV lamp ballasts 132, an electrical distribution block 136, an AC/DC adapter 154, and an ozone pump transformer 138. Electrical distribution block 136 is configured to receive electrical current from an electrical current source via a power cord 134. In the example embodiment, power cord 134 is configured to interface with a U.S. National Electrical Manufacturers Association (NEMA) 5-15 receptacle. In alternative embodiments, power cord 134 is configured to interface with any type of receptacle that enables portable liquid filtration device 100 to function as described herein. In other alternative embodiments, liquid filtration device includes a battery 148 (shown in FIG. 7) located within portable housing 102, or alternatively is coupled to battery 148 located outside housing 102, and electrical distribution block 136 is configured to receive electrical current from battery 148. In yet another alternative embodiment, portable liquid filtration device 100 includes both power cord 134 and battery 148, and portable liquid filtration device 100 is selectively switchable between the power sources. In some embodiments, battery 148 is rechargeable and/or replaceable.

In the exemplary embodiment, electrical distribution block 136 distributes power from the active power source, for example power cord 134 or battery 148, to the various components of filtration device 100. For example, each UV lamp ballast 132 receives electrical current from electrical distribution block 136 and is used to limit the flow of electrical current through each UV lamp 300 (shown in FIG. 6). For another example, ozone pump transformer 138 receives current from electrical distribution block 136 via AC/DC adapter 154 and steps up or down the line voltage to meet the requirements of ozone chamber pump 112 before transmitting the electrical current to ozone chamber pump 112. In alternative embodiments, power is distributed to the components of portable liquid filtration device 100 in any suitable fashion that enables portable liquid filtration device 100 to function as described herein.

Figure 5:
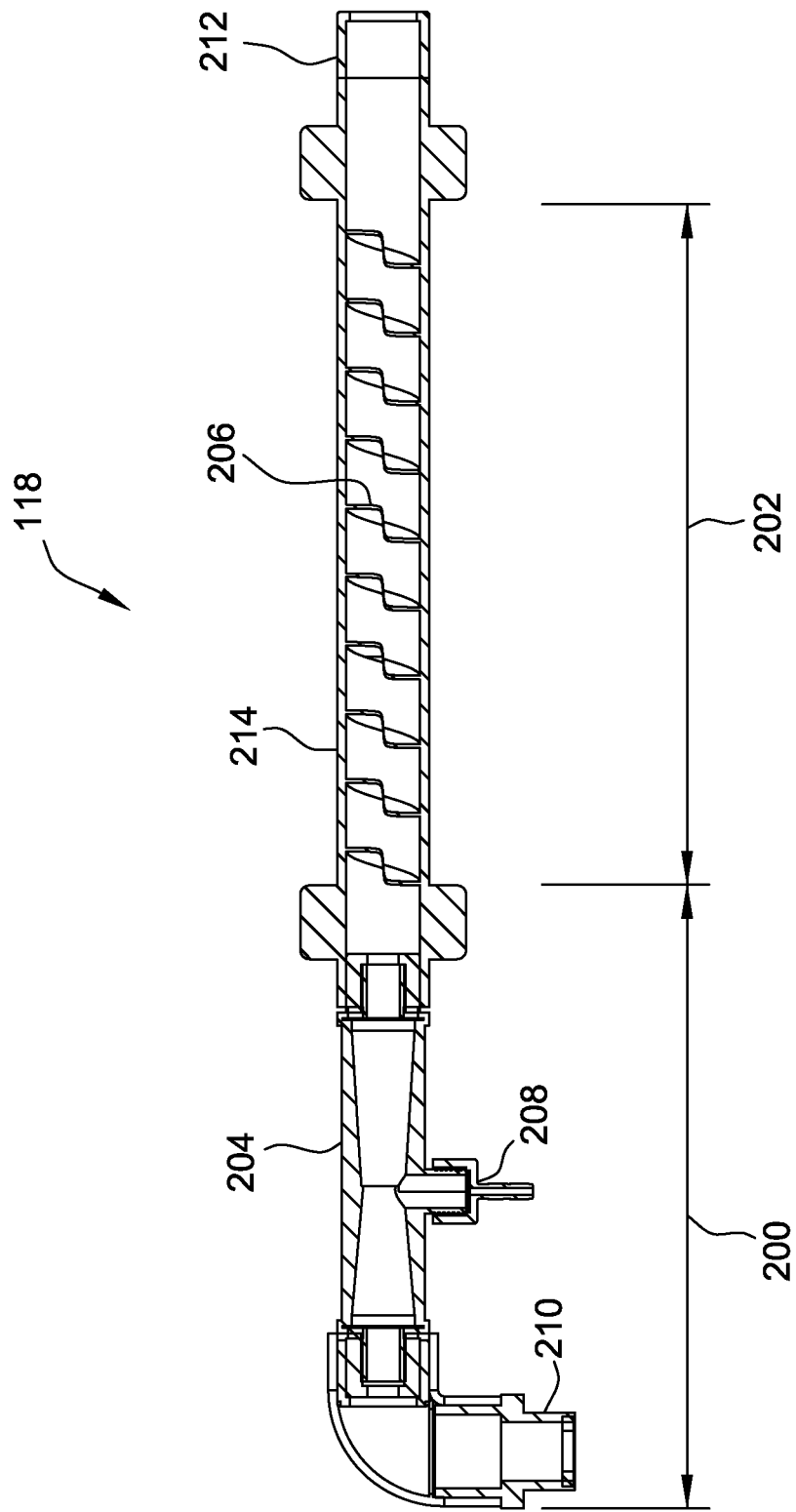
FIG. 5 is a sectional side view of an exemplary advanced oxidation (AO) chamber that may be used with the filtration assembly shown in FIG. 3.

FIG. 5 is a sectional side view of exemplary AO chamber 118 that may be used with filtration assembly 114 (shown in FIG. 3). As described above, AO chamber 118 is configured to mix the non-potable water received from inlet 108 with the ozone gas received from ozone chamber 110. In the exemplary embodiment, AO chamber 118 includes a generally tubular AO chamber body 214 that includes a first mixing portion 200 and a second mixing portion 202 in downstream flow communication with first mixing portion 200. AO chamber 118 is configured to receive water through an AO chamber inlet 210, channel the water serially through first mixing portion 200 and second mixing portion 202, and channel the water out of AO chamber 118 via an AO chamber outlet 212.

In the exemplary embodiment, first mixing portion 200 includes an ozone gas inlet 208 configured to channel the ozone gas from ozone chamber 110 into first mixing portion 200. In the exemplary embodiment, first mixing portion 200 also includes a Venturi nozzle 204 configured to increase a flow speed of the received water proximate to ozone gas inlet 208, such that absorption of the ozone gas by the received water is increased. For example, in some embodiments, a mixing efficiency of first mixing portion 200 is at least 25 percent. In alternative embodiments, AO chamber 118 is configured to receive the ozone gas at any suitable location along AO chamber 118, and/or first mixing portion 200 does not include Venturi nozzle 204.

In the exemplary embodiment, second mixing portion 202 includes a mixing vane 206 configured to facilitate further mixing of the received water with the ozone gas within AO chamber 118. More specifically, in the exemplary embodiment, mixing vane 206 has a helical spiral shape. In alternative embodiments, mixing vane 212 has any suitable shape that enables portable liquid filtration device 100 to function as described herein.

In some embodiments, AO chamber 118 has a length of less than 20 inches. For example, Venturi nozzle 204 has a length of about 5 inches and mixing vane 212 has a length of about 10 inches. In alternative embodiments, each of AO chamber 118, Venturi nozzle 204, and mixing vane 206 has any suitable length that enables portable liquid filtration device 100 to function as described herein.

In alternative embodiments, AO chamber 118 has any suitable number and type of mixing portions that enables portable liquid filtration device 100 to function as described herein.

Figure 6:
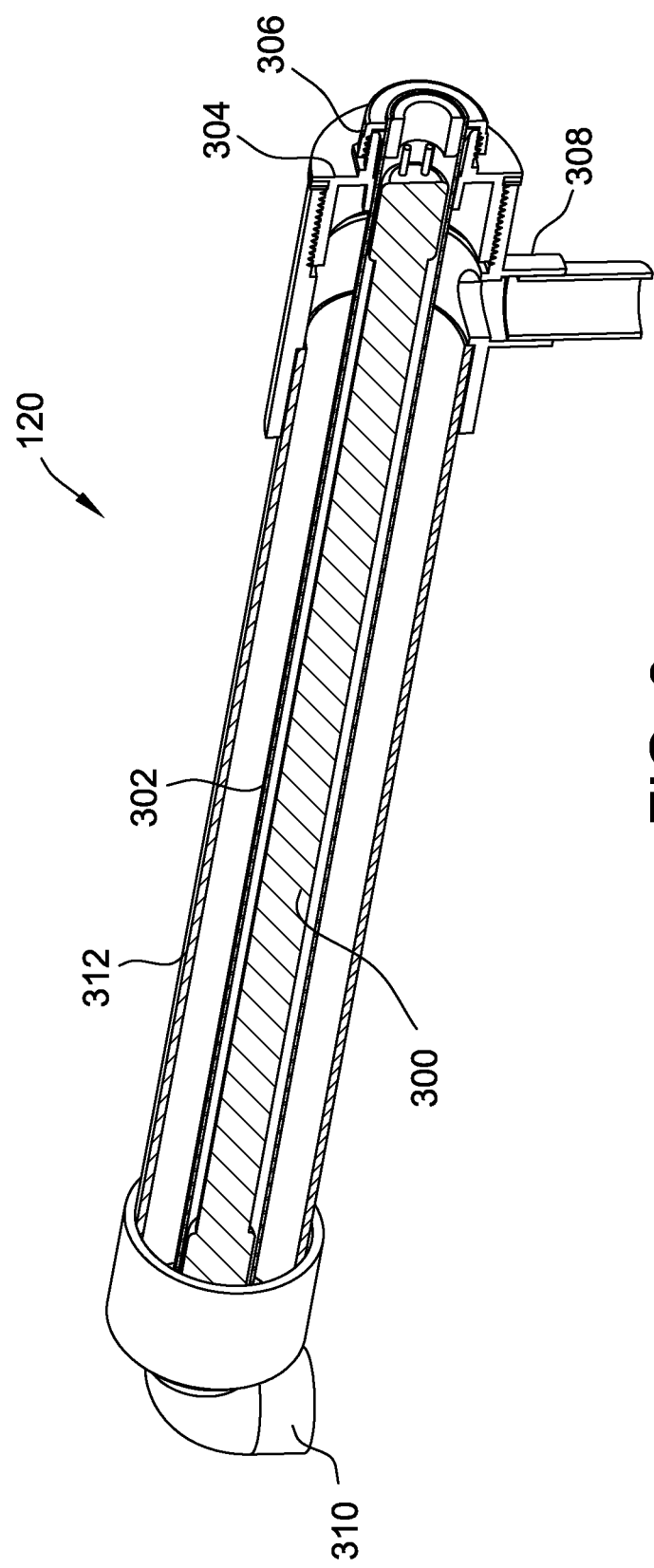
FIG. 6 is a partial sectional side view of an exemplary ultraviolet (UV) chamber that may be used with the filtration assembly shown in FIG. 3.

FIG. 6 is a partial sectional side view of exemplary UV chamber 120 that may be used with filtration assembly 114 (shown in FIG. 3). UV chamber 120 includes a generally tubular body 312 and is configured to receive water through one of a first end 308 and a second end 310, channel the water through body 312, and channel the water out of UV chamber 120 through the other of first end 308 and second end 310. UV chamber 120 also includes a UV lamp 300 positioned adjacent the water flowing through UV chamber 120 and configured to irradiate the water with UV light to facilitate sterilizing organic material suspended within the water.

More specifically, in the exemplary embodiment, tubular body 312 circumscribes UV lamp 300, such that UV light emitted from UV lamp 300 in substantially all directions irradiates the water flowing along an annular path around lamp 300 through UV chamber 120, thus increasing an efficiency of UV chamber 120. For example, UV lamp 300 is located within a substantially translucent UV lamp tube 302 that extends coaxially with, and is circumscribed by, tubular body 312, such that UV lamp 300 is physically isolated from the water flowing through UV chamber 120. In alternative embodiments, UV lamp 300 is positioned with respect to UV chamber 120 in any suitable manner that enables portable liquid filtration device 100 to function as described herein.

Further in the exemplary embodiment, UV chamber 120 includes a UV chamber top cap 304 removably coupled to first end 308 such that UV lamp 300 and UV lamp tube 302 may be withdrawn from UV chamber 120 by uncoupling UV chamber top cap 304 from UV chamber body 312. Additionally, UV chamber 120 includes a UV tube cap 306 removably coupled to UV chamber top cap 304 such that UV lamp 300 may be withdrawn from UV lamp tube 302 by uncoupling UV tube cap 306 from UV chamber top cap 304. In alternative embodiments, UV lamp 300 and/or UV lamp tube 302 are coupled to UV chamber 120 in any suitable fashion that enables portable liquid filtration device 100 to function as described herein. As shown in FIG. 3, in the exemplary embodiment, pair of UV chambers 120 is oriented such that water is channeled serially into second end 310 of a first of UV chambers 120, out of first end 308 of the first of UV chambers 120, into first end 308 of a second of UV chambers 120, and out of second end 310 of the second of UV chambers 120. This orientation facilitates placement of caps 304 and 306 of both UV chambers 120 adjacent to each other while reducing a flow path length between the two, such that UV lamp 300 of both UV chambers 120 may be replaced from the same end of filtration assembly 114. In alternative embodiments, UV chambers 120 are oriented in any suitable fashion that enables portable liquid filtration device 100 to function as described herein.

In some embodiments, each UV chamber 120 has a length of less than 24 inches. In alternative embodiments, each UV chamber 120 has any suitable length that enables portable liquid filtration device 100 to function as described herein.

In certain embodiments, at least one AO chamber 118 (shown in FIG. 5) further includes a separate UV lamp 300 positioned adjacent the water flowing through AO chamber 118, for example coupled to AO chamber 118 as described above with respect to UV chamber 120, or in any other suitable fashion. In some such embodiments, sanitization of the received water is further improved by the additional UV treatment occurring simultaneously with the ozone mixing in at least one AO chamber 118. In other embodiments, AO chamber 118 does include a UV lamp 300 positioned adjacent AO chamber 118.

Figure 7:
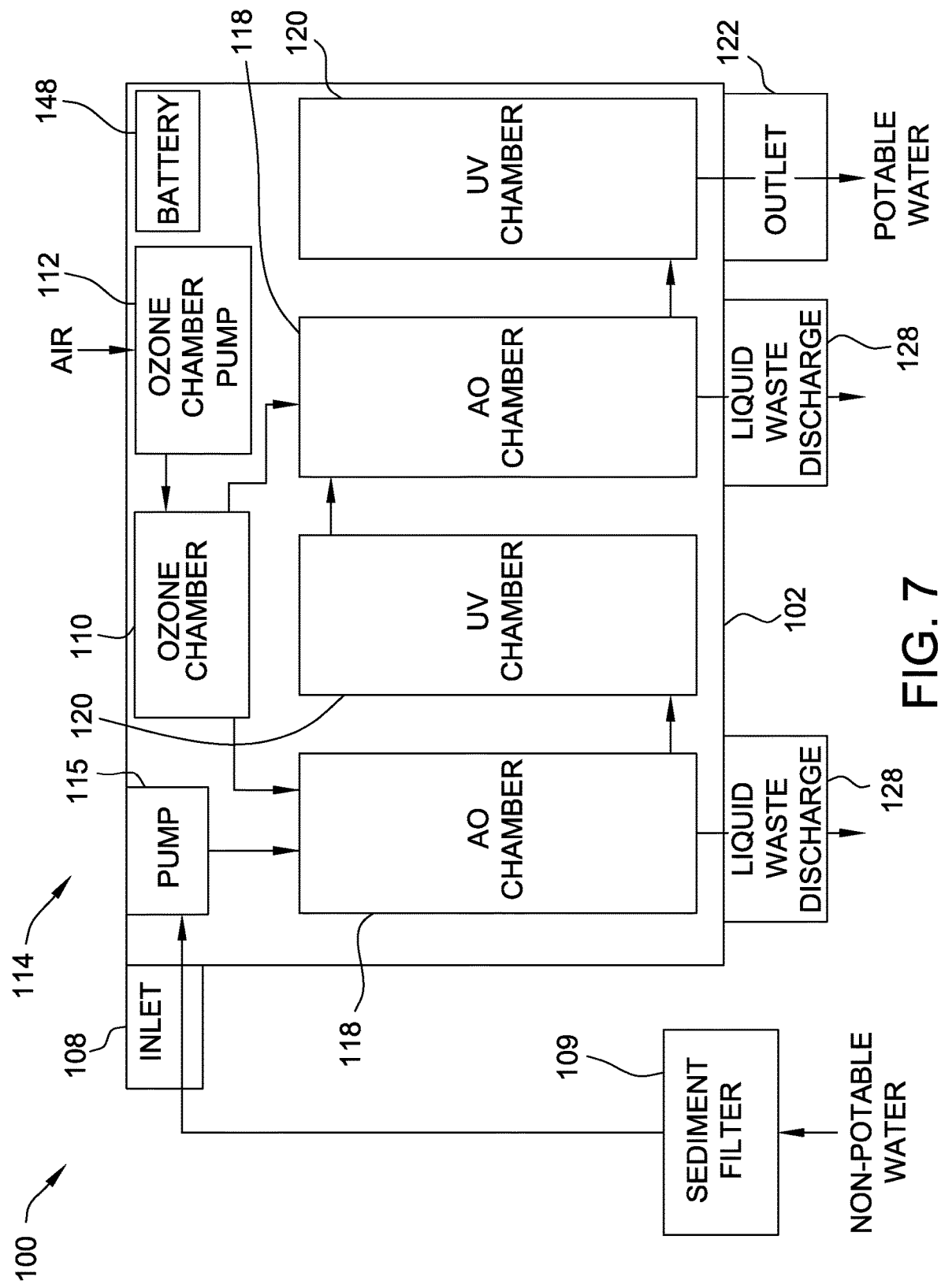
FIG. 7 is a block diagram of an alternative embodiment of the portable liquid filtration device shown in FIG. 1.

FIG. 7 is a block diagram of an alternative embodiment of portable liquid filtration device 100 (shown in FIG. 1) illustrating an alternative filtration assembly 114. The embodiment shown in FIG. 7 is substantially identical to the embodiment shown in FIG. 1, except filtration assembly 114 includes an additional AO chamber 118 as part of filtration duct 116. In addition, the embodiment of FIG. 7 illustrates battery 148 for providing power for operation of portable liquid filtration device 100, as well as the at least one liquid waste discharge port 128. Although battery 148 is illustrated as included within portable housing 102, in alternative embodiments, portable liquid filtration device 100 is coupled to battery 148 located outside and separate from portable liquid filtration device 100.

More specifically, in the exemplary embodiment, filtration duct 116 includes a pair of AO chambers 118 and a pair of UV chambers 120 coupled together in serial flow communication. Ozone chamber 110 is configured channel a first portion of the generated ozone gas to a first of AO chambers 118 and a second portion of the generated ozone gas to a second of AO chambers 118 via parallel flow ozone delivery tubes 152. In alternative embodiments, portable liquid filtration device 100 includes any suitable number of AO chambers 118 and UV chambers 120 that enables portable liquid filtration device 100 to function as described herein.

In the exemplary embodiment, water received through inlet 108 is channeled into the first of AO chambers 118, flows through the first of AO chambers 118, and is channeled to a first of UV chambers 120. The first of UV chambers 120 is in downstream flow communication with the first of AO chambers 118 and receives the water from AO chamber outlet 212. Water flows through the first of UV chambers 120, is irradiated by UV lamp 300, and is channeled out of the first of UV chambers 120. The water is then channeled into a second of AO chambers 118, flows through the second of AO chambers 118, and is channeled into a second of UV chambers 120. Water received by the second of UV chambers 120 flows through the second of UV chambers 120, is irradiated by UV lamp 300, exits the second of UV chambers 120. After the water exits the second of UV chambers 120 the water is discharged through outlet 122 as potable water. In alternative embodiments, portable liquid filtration device 100 includes any suitable arrangement of the components of filtration assembly 114 that enables portable liquid filtration device 100 to function as described herein.

As described above, in some embodiments, waste is generated as the water flows through filtration duct 116, and discharged from at least one liquid waste discharge port 128. In the exemplary embodiment, a first portion of the waste is generated as the water flows through the first of AO chambers 118. The first portion of waste is separated from the primary flow through filtration duct 116, such as by a relatively heavier weight and/or a higher momentum of the waste as the flow turns at the chamber outlet, and is channeled to a first liquid waste discharge port 128 on portable housing 102 for discharge from portable liquid filtration device 100. Similarly, a second portion of waste is generated as the water flows through the second of AO chambers 118, separated from the primary flow through filtration duct 116, and channeled to a second liquid waste discharge port 128 on portable housing 102 for discharge from portable liquid filtration device 100. In alternative embodiments, waste generated as the water flows through filtration duct 116 is separated and discharged from portable liquid filtration device 100 in any suitable fashion that enables portable liquid filtration device 100 to function as described herein. In other alternative embodiments, waste is not generated in sufficient amounts to merit discharge from filtration duct 116.

In some embodiments, as described above, portable liquid filtration device 100 receives power from battery 148. In some such embodiments, operating power requirements of portable liquid filtration device 100 are such that battery 148, implemented as a 12-volt, 300 ampere-hour battery, is sufficient to operate portable liquid filtration device 100 for at least ten hours and/or to produce at least 2,000 total liters of potable water, before battery 148 requires a recharge or replacement. In alternative embodiments, battery 148 operates portable liquid filtration device 100 to produce any suitable amount of potable water over a single charge of battery 148.

With reference to FIGS. 1-7, in certain embodiments, portable liquid filtration device 100 weighs less than 50 pounds, is sized to be received within a volume measuring no more than four cubic feet, and is operable to output at least 200 liters per hour of the received water from outlet 108 as potable water. In some such embodiments, portable liquid filtration device 100 is sized to be received within a volume measuring no more than two cubic feet, further facilitating the transportation of portable liquid filtration device 100 to supply potable water to areas of need. Additionally or alternatively, in some such embodiments, portable liquid filtration device 100 is operable to output at least 400 liters per hour of the received water from outlet 108 as potable water.

Moreover, portable liquid filtration device 100 is of robust construction and operable over a long lifetime. In some embodiments, portable liquid filtration device 100 is operable to produce at least 500,000 total liters of potable water before requiring repair or replacement of any component (other than battery 148, if not recharged). Moreover, in some such embodiments, portable liquid filtration device 100 is operable to produce at least to produce between about 800,000 liters and about 1,000,000 million total liters of potable water before requiring repair or replacement of any component (other than battery 148, if not recharged). In particular, in some such embodiments, portable liquid filtration device 100 is operable to produce about 1,600,000 total liters of potable water before requiring repair or replacement of any component (other than battery 148, if not recharged). In alternative embodiments, portable liquid filtration device 100 is operable to produce any suitable amount of potable water before requiring repair or replacement of any component (other than battery 148, if not recharged).

Thus, portable liquid filtration device 100 has a limited weight and bulk that facilitates transportation of portable liquid filtration device 100 to areas of need, such as by manual transport by a user or small group of users over unimproved terrain if necessary, and also provides a high-volume output that reduces a number of water filtration units needed to meet emergency potable water requirements for a large number of people and/or over a long time period. Moreover, portable liquid filtration device 100 requires no additional assembly or set-up upon arrival at the site of need, but rather is ready to immediately generate potable water. Moreover, operation using replaceable and/or rechargeable battery 148 (shown in FIG. 7), located within portable housing 102 or separately provided, further facilitates use in areas where a power grid is offline or non-existent. In alternative embodiments, portable liquid filtration device 100 has any suitable weight and volume that enables portable liquid filtration device 100 to function as described herein.

The above-described embodiments of portable liquid filtration devices overcome at least some disadvantages of known water purification systems. Specifically, embodiments of the portable liquid filtration device include a portable housing, an inlet and an outlet, an ozone chamber, and a filtration duct including at least AO chamber and at least one UV chamber that cooperate together to sanitize the received water at an output of 200 liters per hour or more. Also specifically, in some embodiments, the device weighs no more than 50 pounds and/or occupies no more than four cubic feet, or even no more than two cubic feet. Also specifically, the device does not require internal filters that have to be replaced on a routine basis and/or that limit the flow rate of water through the portable liquid filtration device. Also specifically, in at least some embodiments, the portable liquid filtration device may be powered by a replaceable or rechargeable battery while producing 2,000 liters of potable water on a single battery charge.

Exemplary embodiments of a portable liquid filtration device, and methods of assembling the same, are described above in detail. The systems and methods are not limited to the specific embodiments described herein, but rather, components of systems and/or steps of methods may be utilized independently and separately from other components and/or steps described herein. For example, the system may also be used in combination with other water purification systems and methods, and is not limited to practice with only a portable liquid filtration device as described herein. Rather, the embodiments can be implemented and utilized in connection with many other liquid purification applications.

Although specific features of various embodiments of the disclosure may be shown in some drawings and not in others, this is for convenience only. Moreover, references to "one embodiment" in the above description are not intended to be interpreted as excluding the existence of additional embodiments that also incorporate the recited features. In accordance with the principles of the disclosure, any feature of a drawing may be referenced and/or claimed in combination with any feature of any other drawing.

This written description uses examples, including the best mode, to illustrate the disclosure and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A portable liquid filtration device comprising:
   a portable housing;
   an inlet positioned on said portable housing and configured to receive non-potable water therethrough;
   an ozone chamber positioned within said portable housing, said ozone chamber configured to receive air from outside said portable housing and generate an ozone gas from the received air via a high voltage discharge into the received air;
   a filtration duct positioned within said portable housing and in downstream fluid communication with said inlet, said filtration duct comprising:
     at least one advanced oxidation (AO) chamber configured to mix the received water with the ozone gas from said ozone chamber, said at least one AO chamber comprising a first AO chamber; and
     at least two ultraviolet (UV) chambers in downstream flow communication with a first of the at least one AO chamber and each comprising a sterilizing UV lamp positioned adjacent the water within the filtration duct;
   an outlet positioned on said portable housing and in downstream flow communication with said filtration duct; and
   a pump positioned within said portable housing and configured to draw in the non-potable water through said inlet and channel the received non-potable water in series to said first AO chamber and said at least two UV chambers at a throughput of at least 200 liters per hour over a one hour period, wherein in response to the received non-potable water having an unknown number and amount of chemical and biological contaminants, said filtration duct is configured to discharge the throughput as potable water from said outlet,
   wherein said portable liquid filtration device is manually transportable by a user, weighs no more than 50 pounds, and is sized to be received within a volume measuring no more than two cubic feet.

2. The portable liquid filtration device according to claim 1, wherein said portable liquid filtration device is operable to output at least 400 liters per hour of the received water from said outlet as potable water.

3. The portable liquid filtration device according to claim 1, wherein said at least one AO chamber further comprises a Venturi nozzle configured to increase a flow speed of the received water such that absorption of the ozone gas by the received water is increased.

4. The portable liquid filtration device according to claim 1, further comprising at least one liquid waste discharge positioned on said portable housing, said at least one liquid waste discharge in downstream flow communication with said at least one AO chamber.

5. The portable liquid filtration device according to claim 1, wherein said at least one AO chamber comprises no more than one AO chamber and said at least two UV chambers comprises no more than two UV chambers, and wherein:
   a first of said UV chambers is in downstream flow communication with said first AO chamber, and
   a second of said UV chambers is in downstream flow communication with said first UV chamber.

6. The portable liquid filtration device according to claim 5, wherein said portable liquid filtration device is operable to output at least 400 liters per hour of the received water from said outlet as potable water.

7. The portable liquid filtration device according to claim 1, wherein said at least one AO chamber comprises no more than two AO chambers and said at least two UV chambers comprises no more than two UV chambers, and wherein:
   said first AO chamber is configured to mix the received water with a first portion of the ozone gas from said ozone chamber,
   a first of said UV chambers is in downstream flow communication with said first AO chamber,
   a second of said AO chambers is in downstream flow communication with said first UV chamber, said second AO chamber configured to mix the received water with a second portion of the ozone gas from said ozone chamber, and
   a second of said UV chambers is in downstream flow communication with said second AO chamber.

8. The portable liquid filtration device according to claim 1, further comprising a mixing vane positioned within said at least one AO chamber, said mixing vane having a helical spiral shape.

9. The portable liquid filtration device according to claim 1, wherein said portable liquid filtration device is operable to output at least 2,000 liters of the received water from said outlet as potable water over a single charge of a 12 volt, 300 ampere-hour battery coupled to the portable liquid filtration device.

10. A method of making a portable liquid filtration device, said method comprising:
   positioning an inlet on a portable housing, the inlet configured to receive non-potable water, the portable housing sized to be received within a volume measuring no more than two cubic feet;

positioning an ozone chamber within the portable housing, the ozone chamber configured to receive air from outside the portable housing and generate an ozone gas from the received air via a high voltage discharge into the received air;

positioning a filtration duct within the portable housing and in downstream fluid communication with the inlet, the filtration duct including:
- at least one advanced oxidation (AO) chamber configured to mix the received water with the ozone gas from the ozone chamber, the at least one AO chamber including a first AO chamber; and
- at least two ultraviolet (UV) chambers in downstream flow communication with a first of the at least one AO chamber and each comprising a sterilizing UV lamp positioned adjacent the water within the filtration duct;

positioning an outlet on the portable housing and in downstream flow communication with the filtration duct; and positioning a pump within the portable housing, the pump configured to draw in non-potable water through the inlet and channel the received non-potable water in series to the first AO chamber and the at least two UV chambers at a throughput of at least 200 liters per hour over a one hour period, wherein in response to the received non-potable water having an unknown number and amount of chemical and biological contaminants, said filtration duct is configured to discharge the throughput as potable water from said outlet;

wherein the portable liquid filtration device is manually transportable by a user, and weighs no more than 50 pounds.

11. The method according to claim 10, further comprising positioning the filtration duct operable to output at least 400 liters per hour of the received water from the outlet as potable water.

12. The method according to claim 10, wherein said positioning the filtration duct within the portable housing comprises positioning the filtration duct including the at least one AO chamber having a Venturi nozzle configured to increase a flow speed of the received water such that absorption of the ozone gas by the received water is increased.

13. The method according to claim 10, further comprising positioning at least one liquid waste discharge on the portable housing, the at least one liquid waste discharge in downstream flow communication with the at least one AO chamber.

14. The method according to claim 10, wherein the at least one AO chamber comprises no more than one AO chamber and the at least two UV chambers comprises no more than two UV chambers, and wherein said positioning the filtration duct within the portable housing comprises:
- coupling a first of the UV chambers in downstream flow communication with the first AO chamber; and
- coupling a second of the UV chambers in downstream flow communication with the first UV chamber.

15. The method according to claim 14, wherein said positioning the filtration duct within the portable housing comprises positioning the filtration duct operable to output at least 400 liters per hour of the received water from the outlet as potable water.

16. The method according to claim 10, wherein the at least one AO chamber comprises no more than two AO chambers and the at least two UV chambers comprises no more than two UV chambers, and wherein said positioning the filtration duct within the portable housing comprises:
- coupling a first of the UV chambers in downstream flow communication with the first AO chamber, wherein the first AO chamber is configured to mix the received water with a first portion of the ozone gas from the ozone chamber;
- coupling a second of the AO chambers in downstream flow communication with the first UV chamber, wherein the second AO chamber is configured to mix the received water with a second portion of the ozone gas from the ozone chamber; and
- coupling a second of the UV chambers in downstream flow communication with the second AO chamber.

17. The method according to claim 10, wherein said positioning the filtration duct within the portable housing comprises positioning the filtration duct including the at least one AO chamber that includes a mixing vane positioned therein, the mixing vane having a helical spiral shape.

18. The method according to claim 10, further comprising sizing an electrical power requirement of the portable liquid filtration device such that the portable liquid filtration device is operable to output at least 2,000 liters of the received water from the outlet as potable water over a single charge of a 12 volt, 300 ampere-hour battery coupled to the portable liquid filtration device.

19. The portable liquid filtration device according to claim 1, wherein said portable liquid filtration device includes no filter housed within said portable housing.

20. The portable liquid filtration device according to claim 1, wherein said portable liquid filtration device further comprises a filter, wherein said filter is external to said portable housing and in upstream flow communication with said inlet via a flexible inlet tube.

* * * * *